Figure 1:
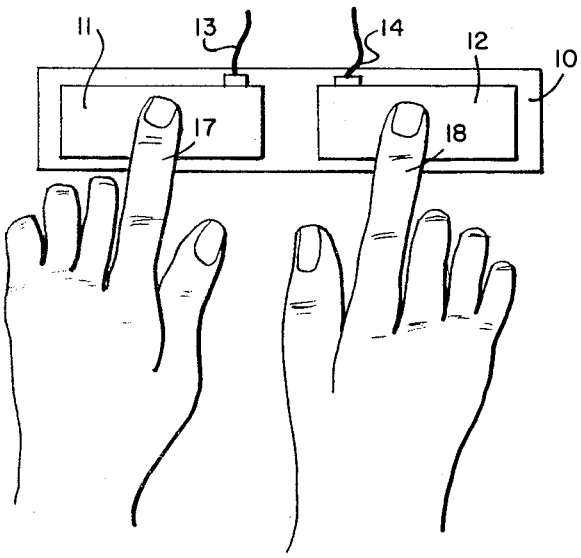
Figure 2:
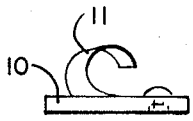
Figure 3:
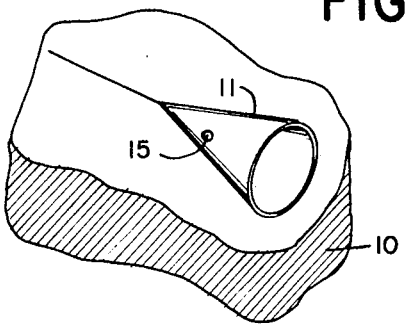
Figure 4:
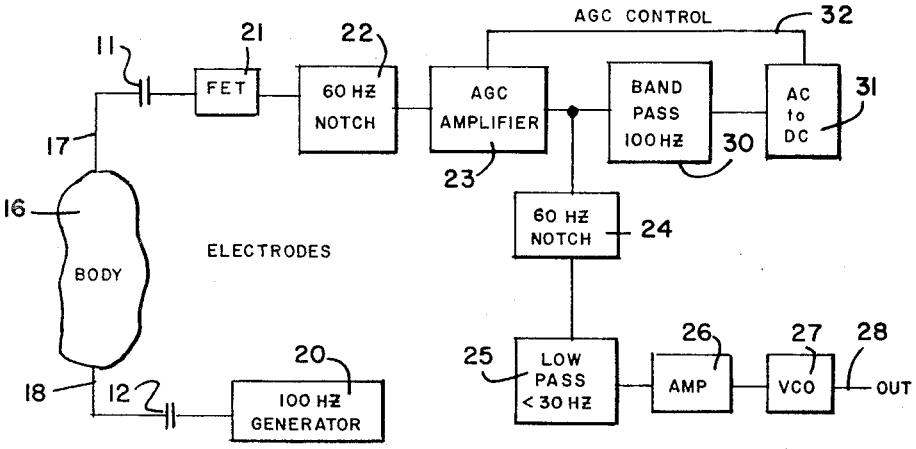
Figure 5:
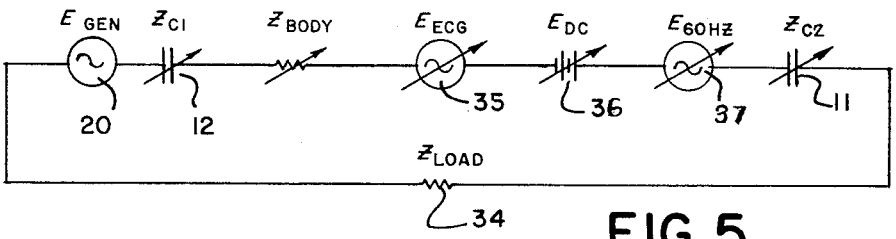

DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED JULY 24, 1973

912 O.G. 1232

T912,010

FINGERTIP EGG MONITOR UTILIZING CARRIER INJECTION FOR AGC

William P. Holsinger, Herndon, Va., assignor to the United States of America as represented by the Secretary of Department of Health, Education, and Welfare Filed May 1, 1972, Ser. No. 249,240
Int. Cl. A61b *5/04*
U.S. Cl. 128—2.06 R
1 Sheet Drawing. 10 Pages Specification

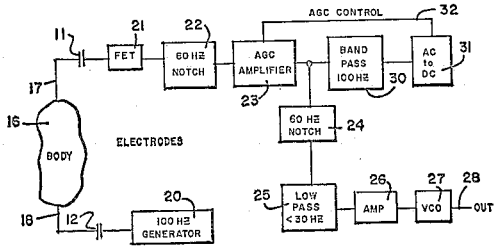

A mass screening system for electrocardiographic abnormalities features a constant 100 Hz. tone generator 20 coupled to the subjects' body via capacitive electrode 12 and a sensing system for picking up the electrocardiographic signal-modified tone including capacitive electrode 11, amplifier 21, 60 cycle filters 22, amplifier 23 and 60 cycle filter 24. The gain of amplifier 23 is automatically controlled by a feedback loop which has a filter 30 to eliminate all but the tone whose fluctuating amplitude is then converted to a D.C. control signal by converter 31 and introduced via lead 32 into the amplifier to adjust the gain thereof. At the output of the 60 cycle filter 24, a low pass filter 25 is provided to remove the 100 Hz. tone from the electrocardiographic information. The information is then amplified in amplifier 26 and used as a modulating signal for the variable frequency oscillator 27 resulting in a frequency modulated signal at 28 for transmission, over telephone lines for example, to a remote monitoring station.

FINGERTIP EGG MONITOR UTILIZING CARRIER INJECTION FOR AGC

Filed May 1, 1972